US00RE34349E

United States Patent [19]

Unruh et al.

[11] E Patent Number: Re. 34,349

[45] Reissued Date of Patent: Aug. 17, 1993

[54] METHOD FOR THE MANUFACTURE OF 1,3-PROPANEDIOL

[75] Inventors: Jerry D. Unruh; Debra A. Ryan; Ioan Nicolau, all of Corpus Christi, Tex.

[73] Assignee: Hoechst Celanese Corporation, Somerville, N.J.

[21] Appl. No.: 869,572

[22] Filed: Apr. 15, 1992

Related U.S. Patent Documents

Reissue of:

[64] Patent No.: 5,093,537
Issued: Mar. 3, 1992
Appl. No.: 735,391
Filed: Jul. 24, 1991

[51] Int. Cl.[5] ..... C07C 29/141; C07C 31/20; C07C 45/42; C07C 47/19

[52] U.S. Cl. ..... 568/862; 568/458

[58] Field of Search ..... 568/491, 458, 862

[56] References Cited

U.S. PATENT DOCUMENTS

| | | | |
|---|---|---|---|
| 3,260,759 | 7/1966 | Skinner | 508/862 |
| 3,518,310 | 6/1970 | Lutz | 568/862 |
| 3,536,763 | 10/1970 | Electerio et al. | 568/458 |
| 5,015,789 | 5/1991 | Arntz et al. | 568/862 |

*Primary Examiner*—Joseph E. Evans
*Attorney, Agent, or Firm*—Donald R. Cassady

[57] ABSTRACT

1,3-Propanediol is manufactured by the hydration of acrolein in an aqueous solution over a fully hydrated, alumina-bound zeolite with a pore size >5 angstroms to form 3-hydroxypropanal and hydrogenation of the 3-hydroxypropanal typically in an aqueous solution in the presence of a nickel catalyst.

10 Claims, No Drawings

METHOD FOR THE MANUFACTURE OF 1,3-PROPANEDIOL

Matter enclosed in heavy brackets [ ] appears in the original patent but forms no part of this reissue specification; matter printed in italics indicates the additions made by reissue.

BACKGROUND OF THE INVENTION 1,3-Propanediol (PDO) is a potentially attractive comonomer for a polyester, poly (1,3-propyl terephthalate) (PPT) which is particularly valuable as a superior carpet fiber. There is also commercial interest in the glycol as a multiple functional small molecule.

Typical of these applications is as a monomeric component for polyurethanes, and as a component in many cyclic compounds. Many methods have already been suggested for the synthesis of PDO, including synthesis from ethylene oxide and carbon monoxide catalyzed by rhodium and a co-catalyst and by the hydration of acrolein and hydrogenation of the resulting 3-hydroxypropanal. Acrolein is a readily available reactive organic compound.

U.S. Pat. No. 2,434,110 discloses that acrolein can be hydrated in the presence of an acidic catalyst to form 3-hydroxypropanal (HPA). The reaction preferably takes place at an elevated temperature using 5–30 wt. % solution of acrolein in water and an acid, as for example, sulfuric acid, phosphoric acid, or the acid salts of these acids as the catalyst. The reaction mixture obtained during the hydration is then hydrogenated in the presence of an active hydrogenation catalyst, as for example Raney nickel. A disadvantage of the process described is the low yield of HPA attributable to the condensation reactions which occur concurrently to the hydration.

U.S. Pat. No. 3,536,763 describes the hydration reaction as being carried out in the presence of a weakly acidic cation exchange resin the functional groups being carboxylic acids. The reaction occurred at from 40°–120° C. Preferably about 0.1 to about 5% of the carboxyl groups are present in the form of the alkali carboxylate, alkaline earth carboxylate, or earth metal carboxylate.

Recent patent activity demonstrates that there is still considerable interest in improving the traditional methods of the manufacture of PDO. One of these improvements has been disclosed in U.S. Pat. Nos. 4,873,378, 4,873,379, and 4,935,554 which disclose methods to produce PDO in one step by ethylene oxide carbonylation using a rhodium catalyst.

Degussa, in U.S. Pat. No. 5,015,789, describes the acrolein hydration/hydrogenation route to PDO using an acidic cation exchange resin containing phosphonic acid groups in the acid or salt form as a catalyst to cause the hydration of acrolein and separation of the catalyst and unreacted acrolein. This is followed by a conventional hydrogenation reaction of the HPA.

SUMMARY OF THE INVENTION

It is the purpose of the present invention to describe and claim the production of HPA over a solid zeolite catalyst so that the aqueous HPA solution is neutral and contains no salts after exiting the reactor and to hydrogenate the aqueous solution with no other treatment than removing excess acrolein. According to the method of the present invention, acrolein is hydrated in aqueous solution in the presence of a hydrated alumina-bound zeolite catalyst of pore size greater than 5 angstroms containing an alumina binder, the resulting aqueous solution, after removal of any unreacted acrolein, is hydrogenated in the presence of an appropriate hydrogenation catalyst according to those methods known in the art. Raney nickel is the preferred catalyst for the hydrogenation. The reaction sequence is shown below.

$$CH_2{=}CHCHO + H_2O \xrightarrow{\text{zeolite}} HOCH_2CH_2CHO$$

$$HOCH_2CH_2CHO + H_2 \xrightarrow{\text{Raney Ni}} HOCH_2CH_2CH_2OH$$

Most of the unwanted by-products arise from HPA reacting with itself to form HPA dimer or with acrolein to form a variety of higher molecular weight compounds. Acrolein can also react with itself to form the so-called thermal dimer. The hydrated alumina-bound zeolites as catalysts reduce significantly the ability for these secondary reactions of HPA to occur.

According to the method of this invention the following results can be obtained in the hydration of acrolein and subsequent hydrogenation of the HPA after removal of the unreacted acrolein.

40–60% conversion of acrolein per pass through the reactor.

99% recovery of the unconverted acrolein for recycle back to the reactor. Therefore, 99% conversion of acrolein.

86–90% selectivity of acrolein to HPA.

8–12% HPA in solution after removal of acrolein.

The keys to high selectivity to HPA appear to be the following.

Apparent shape selective catalysis by the zeolite catalyst.

Presence of water molecules within the pores of the catalyst.

Absence of catalyst, catalyst salts or other extraneous materials, once the crude aqueous HPA leaves the reactor. This allows easy, efficient removal of the unconverted acrolein and relatively stable solutions as long as they are kept cold (<5° C.).

DETAILED DESCRIPTION OF THE INVENTION

Acrolein can be hydrated both non-catalytically and catalytically in the presence of acids. In general the selectivity is only about 50–65% if there is enough conversion of acrolein to have a reasonable amount of HPA in solution. Selectivities reported herein are normalized. Generally speaking there is either insufficient conversion or selectivity to HPA or both. This is true whether soluble acids or acid ion exchange resins are used. We have found an exception to this using certain hydrated, alumina-bound, zeolite catalysts which have pore sizes >5 angstroms. These produce HPA at significantly higher selectivities (85–90%) at reasonable rates. Specific examples of these hydrated, alumina-bound zeolites are a ZSM-5 type catalyst, as for example, "MFI" from UOP, with a silica:alumina ratio of 32–38, and pore openings of about 5.8 angstroms, LZM-8, also from UOP, a synthetic mordenite with pore openings of about 7.8 angstroms and LZY-84, a Y-zeolite with a pore size of about 7 angstroms. Although we do not wish to be bound to the explanations offered herewithin, we offer them with the intent to attempt to explain the phenomenon we observed during the reduction to practice of the invention. We believe that the alumina is somehow pre-activating the acrolein or water prior to entry into the zeolite pore. We also believe that the reason for this improved selectivity is due to the shape selectivity imposed by the zeolite and a synergy between the alumina binder and the zeolite.

According to the method of the present invention the catalyst is washed well with water to saturate its pores. Acrolein and water are then supplied to the catalyst either batch-wise or in a continuous manner. The preferred weight ratio of water to acrolein is from about 2 to 1 to about 20 to 1. The most preferable range is from about 4:1 to about 10:1. The temperature of the reactor to cause hydration to occur can be from about ambient room temperature to about the boiling point of the reaction mixture. Reaction temperatures of below 50° C. cause a very slot reaction rate while temperatures above 100° C. cause reduced selectivity. For that reason, the preferred reaction temperature is from about 50° C. to about 100° C. At the preferred temperatures the reaction is run at greater than atmospheric pressure in order to keep the reactants in a liquid state to minimize the loss of acrolein by evaporation.

If desired, polymerization inhibitors such as for example hydroquinone, hydroquinone monomethyl ether, or the like can be added to the acrolein-water mixture in an effective amount to reduce the polymerization of acrolein without inhibiting the desired hydration reaction.

The reaction can be carried out continuously or discontinuously in agitated or stirred vessels, in straight through tube or loop reactors. The rate of flow through the reactor can be adjusted to maximize conversion and selectivity at a given temperature and acrolein concentration.

The catalyst is removed from the reaction mixture by physical separation, decantation, filtration, or the like and the resulting aqueous solution is freed from unconverted acrolein. This separation is always recommended since the acrolein can be returned to the reactor. The separation can be carried out in a manner well-known to the art, especially by distillation. Particularly useful is distillation at reduced pressure with limited contact time between the liquid and the heat source to minimize decomposition of the organic components of the solution. Of particular value in carrying out the distillation is the use of the thin-film or wiped-film evaporator. Using such an apparatus, an aqueous solution of HPA is the residual material which can be hydrogenated without further treatment.

The catalytic hydrogenation of the HPA is carried out in the liquid phase in aqueous solution in a known manner in typical hydrogenation reactors. The catalyst can be present in suspended form or can be supported or can be a part of or component of a fixed-bed catalyst. Particularly suitable catalysts are, for example, Raney nickel, supported nickel, and palladium on carbon. Hydrogenations are usually carried out at from about 25° C. to about 125° C. with the aqueous solution of HPA recovered from the removal of catalyst and acrolein.

The following examples demonstrate the excellent conversions and selectivities obtained over extended periods of continuous runs using several catalysts within the group contemplated by this invention. The examples are for illustrative purposes only and are not meant to limit the invention thereto.

EXAMPLES

Continuous studies were carried out in a continuous flow reactor. The catalyst charges were as follows:

1) MFI/alumina bound, 14/16 mesh particles;

2) MFI/alumina bound, mixed particle size, 14/16 and 35/40 mesh;

3) MFI/alumina bound, 18/20 mesh particles;

4) MFI/alumina bound, mixed mesh, 14/16 and 35/40 using catalyst from 1) and 2) above;

5) LZM-8/alumina bound, mixed particle size, 14/16 and 35/40 mesh.

The reactor consisted of a jacketed 1 inch inside diameter stainless steel tube 7 feet long. The internal volume was about 1250 ml. Tempered water was used to heat the reactor. The tempered water consisted of a steam bucket and a chilled water bucket. Temperature was controlled by a motor-valve on the chilled water supply line with the control point at the middle thermocouple in the reactor. Generally, temperature only varied by 2° C. in the column. A differential pressure cell was used to control the level of the reactants in the reactor. A back-pressure regulator was used to control pressure. It was noted that pressure was not an important variable as long as it was high enough to keep the acrolein from evaporating. Aqueous solutions of acrolein at the desired concentration were pumped into the bottom of the column at the desired rate (determined by weight), while the crude reaction mixtures were removed from the top by the level controller. The crude reaction mixtures were immediately conducted to chilled receiver. Stream samples were taken at intervals for analysis; a composite sample was taken whenever the receivers were changed. A final important point is that the catalysts were always washed with several gallons of water after they were charged. Therefore, the catalysts were always water full before introduction of any acrolein. Water was fed with the acrolein in at least a 6-fold molar excess. After the product was removed from the reactor, unreacted acrolein was removed in a wiped-film evaporator and was recycled. Since the production of the HPA occurs with a heterogeneous catalyst, the crude reaction mixture contained no extraneous substances when it exited the reactor. This fact makes removal of the acrolein efficient and simple. As long as this reaction mixture is kept cold (below about 5° C.), it was relatively stable and could be stored for several weeks before or after acrolein removal with no noticeable deterioration. However, at room temperature or above, we observed changes in a day and sometimes in a matter of several hours. It is undoubtedly important to use a minimum residence time distillation system in order to minimize the time the solutions spend at high temperatures.

The following results were obtained in the five continuous runs identified above while varying conditions with the run, over extended periods of time using different catalysts either in mesh size or in composition.

1) MFI/alumina bound, 14/16 mesh particles. The unit was run 24 hours/day 5 days/week for 15 weeks. Thus, the catalyst was exposed to acrolein at operating temperatures for approximately 100 hours/week or a total of about 1500 hours with little if any observable catalyst deactivation. The residence time reported is the actual liquid residence time determined by the void volume of about 600 ml. The space-time yield (STY) in (g/L.hr of catalyst) is based on catalyst charge. It is based on actual weight of product obtained and on the amount of HPA in the composite sample. During that period of time that the reactor was at 80° C. and 18-19% acrolein, the percent conversion of acrolein averaged 44.3% with the selectivity to HPA at 87.7% with over 98% of the acrolein being accounted for. With residence times in the 2-3 hour range the HPA selectivity was in the 86-90% range averaging 87.7%, with 7-10% HPA in the crude product. The acrolein conversion with 35-45% averaging 44.27%. The STY was 14-18 g/L.hr depending on feed rate. The mass accountability was 98-100% and the gas-liquid chromatography accountability was 95-110%. Reducing the concentration of acrolein in the feed below 18% stepwise to about 12 wt. % increased the conversion to 46.0% and the selectivity to 91.7%. The STY was reduced to 12 g/L.hr. Decreasing the acrolein concentration to 6 wt. % and the residence time to 8.2 hours increased the conversion to 77% but decreased the selectivity to 73%. At least semi-quantitatively, the response to acrolein is first order. Hence, lower acrolein feed concentrations lead to lower STY's. The selectivity is a function of both the residence time and the amount of HPA in the product. Compared to the 18% acrolein runs, the selectivities are lower for a given amount of HPA in the product because the residence times need to be longer to obtain the higher acrolein conversions. When the solubility limit of acrolein in the feed (20%) was exceeded, i.e., up to 30%, by mixing aqueous acrolein with 97% acrolein the STY's were in the same range (16.3-21 g/L.hr) as for the 18% acrolein runs. The 97% acrolein and aqueous acrolein were co-fed in order to obtain reactor feed which had acrolein concentrations of 30% (a static mixer between the reactor and the feeds was used to mix the two streams). Unlike the apparent first order kinetic response observed in the runs shown in the 18% runs the reaction appeared to be approximately zero order in acrolein above 18% acrolein. When the temperature of the reactor was reduced to 70° C. or increased to 100° C. the conversions and selectivities were no better than the results obtained at 80° C. Apparently, any presumed gain in selectivity due to the lower temperature was offset by the increased residence time necessary to obtain the desired conversion.

2) MFI/alumina bound, Mixed Particle size 14/16 mesh and 35/40 mesh. The purpose of this run was to increase catalyst loading and surface area in the reactor. It was an attempt to determine the effect of the pore size and the interparticle surface area on the reaction, particularly on the selectivity to HPA and acrolein conversion rates. Early evidence indicated that the hydration occurred in the pores while heavy ends formation occurred in the interstitial space between the catalyst particles. The catalyst was exposed to acrolein for 600-700 hours. During that time there was no obvious drop in activity. At comparable temperatures and residence times, the conversion of acrolein was much higher (the reaction was much faster) and the HPA selectivity was much lower. At an acrolein concentration of 18 wt. %, a residence time of about 2 hours at 80° C., the conversion ranged from 64-82% with the selectivity falling to 63-77%. The STY was in the range of 32 g/L.hr. Ultimately an HPA selectivity of 88-90% was attained by reducing the concentration of acrolein in the feed to 15 wt. %.

3) MFI/Alumina Bound; 18/20 Mesh Particles. Given the smaller particle size in this variant, we initially thought that the STY would be higher so that a lower operating temperature could be used. Presumably, this would lead to higher HPA selectivities. Accordingly, the experiments on this catalyst were started at 60° C. and 15% acrolein in the feed. While the HPA concentration was in the expected range, the HPA selectivifies were disappointingly low at 82-85%. The temperature was then raised from 60° to 80° C. in order to improve the HPA selectivities. The selectivities remained low except at 70° C. In this case, HPA selectivities of 86-88% were obtained with HPA concentrations in the 7-9% range. The STY was only about 22 g/L.hr which was not much higher than found in catalyst variant 1. Once again the apparent optimum temperature is near 80° C. where the HPA concentrations are about 8%, the HPA selectivities are 86-88%, and the STY's are 38-39 g/L.hr.

4) MFI/Alumina Bound, Mixed Mesh, 14/16 and 35/40, (Cat. from 1) and 2) above). Catalyst particles from Runs 1) and 2), which had been previously dried at about 110° C., were resieved. The two particle sizes were mixed in a tumbler in order to obtain better mixing than in catalyst variant 2; the catalyst so obtained was charged to the reactor. The results of an approximately 100 hour study demonstrated that the catalyst was still active and provided the same results, within experimental error, as catalyst variant 2, i.e., 7-9% HPA in the reactor effluent, 86-88% HPA selectivities, and STY's of 20-30 g/L.hr.

5) LZM-8/Alumina Bound, Mixed particle size, 14/16 and 35/40 mesh. A two-week run was made with this catalyst. With this catalyst is found the familiar trade off between HPA concentration in the effluent and HPA selectivity. At 80° C., 86-88% HPA selectivities were obtained at 15 wt. % acrolein. The most interesting feature of this catalyst, however, was the fact that it appears more active than MFI with STY's in the 45-50 g/L.hr range. Contrary to MFI, however, the optimum temperature for this catalyst may be about 60° C. rather than 80° C.

BATCH EXAMPLE

The above-identified catalysts were used in batch operations to hydrate acrolein to HPA. Using comparable temperatures and concentrations, similar results were obtained as in the continuous runs reported. In addition, another alumina-bound zeolite catalyst denominated LZY-84, from UOP, was used in batch operations. The results were as follows:

| Temp. (°C.) | Time (hr) | Wt. % Acrolein | % Conversion | Selectivity |
|---|---|---|---|---|
| 60 | 4 | 17.32 | 59.35 | 70.5 |
| 50 | 4 | 16.83 | 40.70 | 94.3 |

As a result of the experimentation the following general observations were made.

There are strong interactions between reactor temperature and acrolein residence time.

To a lesser extent, there were interactions between initial acrolein concentration and the other two variables.

Under most conditions the reaction appeared first order in acrolein.

Since most of the by-products arise from secondary reactions of HPA with itself or with acrolein, HPA selectivity is generally inversely correlated with the amount of HPA in solution.

Because there is a balance between conversion of acrolein, rate of hydration, and selectivity to HPA, there are optimum conditions of temperature, residence time, and initial acrolein concentration which lead to the optimal selectivity to HPA (85-90%) and HPA concentration (7-10%) HPA in solution). The optimal temperature range for carrying out the present invention is from about 60° C. to about 100° C. For the method of the present invention the preferable temperature is about 60° C. to about 80° C. The residence time and initial acrolein concentration was variable depending on which catalyst variant was being tested. With all of the catalyst variants we noticed the general trend that HPA selectivity is inversely proportional to the concentration of HPA. However, as a general rule, concentrations of acrolein below 10 wt. % were not economical while concentrations above the solubility of acrolein (20 wt. %) showed no greater conversions than at the saturation concentration. More HPA was, however, found in the final solution. As the concentration of acrolein increased, however, the residence time increased, lowering selectivity and the concentration of by-products.

HYDROGENATION EXAMPLES

EXAMPLE 1

An aqueous solution from acrolein hydration was concentrated by water removal under vacuum to contain ~20 wt. % HPA. 160 g of this solution was charged to a 500 cc stainless steel autoclave. The autoclave already contained 9.4 g of molybdenum promoted Raney nickel catalyst of ~50μ particle size and 4 g of diatomaceous earth wet with aqueous PDO from a prior HPA hydrogenation. The autoclave was sealed, purged with nitrogen, and then hydrogen. Stirring was initiated, and the autoclave was heated to 40° C. The autoclave pressure was adjusted with hydrogen to 250 psig total. The reaction pressure was maintained constant throughout the hydrogenation by supplying hydrogen upon demand. Hydrogen uptake ceased in 85 minutes, and then the autoclave was cooled, vented, purged with nitrogen, and the aqueous PDO filtered in situ while exiting the autoclave through a sample tube. The product stream was analyzed by GC to be 19.7 wt. % PDO, 1.0 wt % HPA, and ~3 wt. % of other species. This corresponds to an HPA conversion of 95% with a selectivity of virtually 100%.

EXAMPLE 2

A similar solution as in Example 1 was concentrated by water removal under vacuum to contain ~14 wt. % HPA. 155 g of this solution was charged to the autoclave which contained 9.4 g of molybdenum promoted Raney nickel catalyst of ~50μ particle size and 4 g of diatomaceous earth wet with aqueous PDO from a prior HPA hydrogenation. After the same start-up procedure as in Example 1, the autoclave was heated to 95° C. and the hydrogen pressure again adjusted to 250 psig total. The hydrogen uptake ceased in 45 minutes, and the product stream was removed from the autoclave as in Example 1. The GC analysis of the product stream showed a 11.4 wt. % PDO, 1.2 wt. % propanol, 0.2 wt. % HPA, and ~1.5 wt. % of other species. This corresponds to an HPA conversion of 99% with a selectivity of 81% to PDO.

EXAMPLE 3

Another solution from acrolein hydration was concentrated by water removal under vacuum to contain ~13 wt. % HPA. 160 g of this solution was charged to the autoclave which contained 9.4 g of molybdenum promoted Raney nickel catalyst of ~50μ particle size and 4 g of diatomaceous earth wet with aqueous PDO from a prior HPA hydrogenation. After the same start-up procedure as in Example 1, the autoclave was heated to 95° C. and the hydrogen pressure adjusted to 800 psig total. The hydrogen uptake ceased in 15 minutes, and the product stream was removed from the autoclave as in Example 1. The GC analysis of the product stream showed 10.4 wt. % PDO, 1.4 wt. % propanol, 0.3 wt. % HPA, and ~2 wt. % other species. This corresponds to an HPA conversion of 97% with a selectivity of 78% to PDO.

EXAMPLE 4

A similar solution to the one in Example 1 was concentrated by water removal under vacuum to contain ~10 wt. % HPA. 136 g of this solution was charged to the autoclave described in Example 1, containing 7.4 g of Raney nickel (no diatomaceous earth), wet with 6.3 g of water. After the same start-up procedure as in Example 1, the autoclave was heated to 50°-55° C. and the hydrogen pressure was adjusted to 300 psig total. The hydrogen uptake ceased after 39 minutes and the product stream was analyzed by GC to be 8.7 wt. % PDO, <0.01 wt. % propanol, 0.3 wt. % HPA, and ~1.5 wt. % other species. This corresponds to an HPA conversion of 95% with a selectivity of 93% to PDO.

What is claimed is:

1. In a method for the manufacture of 1,3-propanediol which comprises [hydrolyzing] *hydrating* acrolein in an aqueous solution to form 3-hydroxypropanal, removing the unreacted acrolein, and hydrogenating the resulting aqueous solution of 3-hydroxypropanal to form 1,3-propanediol, the improvement which comprises carrying out the [hydrolysis] *hydration* in the presence of a hydrated, alumina-bound zeolite with a pore size >5 angstroms.

2. The method of claim 1 wherein the [hydrolysis] *hydration* is carried out at from about 50° C. to about the boiling point at about the pressure of the reaction.

3. The method of claim 1 wherein the [hydrolysis] *hydration* is carried out with an aqueous solution of acrolein consisting essentially of water and acrolein in a weight ratio of from about 2:1 to about 20:1.

4. The method of claim 1 wherein the hydration is carried out in a continuous manner.

5. The method of claim 4 wherein the [hydrolysis] *hydration* is carried out at from about 50° C. to about 100° C.

6. The method of claim 4 wherein the [hydrolysis] *hydration* is carried out with an aqueous solution consisting essentially of water and acrolein in a weight ratio of from about 2:1 to about 20:1.

7. The method of claim 6 wherein the [hydrolysis] *hydration* is carried out at from about 50° C. to about 100° C.

8. The method of claim 1 wherein the hydrogenation is carried out in the presence of Raney nickel.

9. The method of claim 4 wherein the hydrogenation is carried out in the presence of Raney nickel.

10. The method of claim 6 wherein the hydrogenation is carried out in the presence of Raney nickel.

* * * * *